United States Patent
Schmidt

(10) Patent No.: US 7,524,973 B2
(45) Date of Patent: Apr. 28, 2009

(54) NITRATE ESTERS OF PHENYLAMINOTHIOPHENACETIC ACID DERIVATIVES

(75) Inventor: Beate Schmidt, Allensbach (DE)

(73) Assignee: Altana Pharma AG, Konstanz, DE (US)

( * ) Notice: Subject to any disclaimer, the term of this patent is extended or adjusted under 35 U.S.C. 154(b) by 206 days.

(21) Appl. No.: 10/545,414

(22) PCT Filed: Feb. 17, 2004

(86) PCT No.: PCT/EP2004/050144

§ 371 (c)(1),
(2), (4) Date: Sep. 20, 2005

(87) PCT Pub. No.: WO2004/074271

PCT Pub. Date: Sep. 2, 2004

(65) Prior Publication Data

US 2006/0167082 A1    Jul. 27, 2006

(30) Foreign Application Priority Data

Feb. 19, 2003    (EP) .................... 03003731

(51) Int. Cl.
*C07D 333/36*    (2006.01)
(52) U.S. Cl. ...................................... 549/68
(58) Field of Classification Search ............. 549/68
See application file for complete search history.

(56) References Cited

U.S. PATENT DOCUMENTS

| 4,272,507 A | 6/1981 | Figala |
| 5,700,947 A | 12/1997 | Soldato |
| 2003/0007931 A1* | 1/2003 | Hafner ................. 424/45 |

FOREIGN PATENT DOCUMENTS

| WO | 95/09831 A1 | 4/1995 |
| WO | 01/45703 A1 | 6/2001 |

OTHER PUBLICATIONS

Medical Encyclopedia: Zollinger-Ellison syndrome [online], [retrieved on Aug. 27, 2007]. Retrieved from the Internet, URL; http://www.nlm.nih.gov/medlineplus/print/ency/article/000325.htm>.*
Obach, R. Drug-Drug Interactions: An Important Negative Attribute in Drugs. Drugs of Today. (2003), 39, 301-338.*
Cancer and Metastasis Reviews (1998),17(1), 91-106.*
Science (1999), vol. 286, 531-537.*
Cancer [online], [retrieved on Jul. 6, 2007]. Retrieved from the Internet, URL; http://www.nlm.nih.gov/medlineplus/cancer.html>.*
Cancer [online], [retrieved on Jul. 6, 2007]. Retrieved from the Internet, URL; http://en.wikipedia.org/wiki/Cancer>.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/condtions/09/24/alzheimers.drug.ap/indexhtml>.*
Lupus erythematosus [online], [retrieved on Dec. 28, 2006]. Retrieved from the Internet, URL; http://en.wikipedia.org/wiki/Lupus_erythematosus>.*
Vippagunta, et al. Advanced Drug Delivery Reviews. 48 (2001) 3-26.*
FitzGerald, "COX-2 and Beyond: Approaches to Prostaglandin Inhibition in Human Disease", Nature Rev. Drug Disc. 2:879-890 (Nov. 2003).

* cited by examiner

*Primary Examiner*—Rei-Tsang Shiao
*Assistant Examiner*—Shawquia Young
(74) *Attorney, Agent, or Firm*—The Nath Law Group; Joshua B. Goldberg; Sheldon M. McGee

(57) ABSTRACT

The compounds of formula I

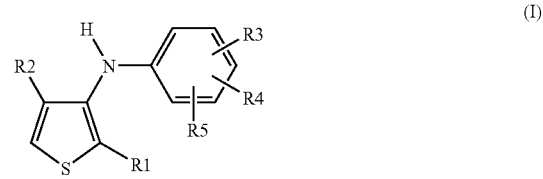

(I)

in which R1, R2, R3, R4 and R5 have the meanings as given in the description are novel effective antiinflammatory compounds.

7 Claims, No Drawings

NITRATE ESTERS OF PHENYLAMINOTHIOPHENACETIC ACID DERIVATIVES

The invention relates to novel nitrate esters of derivatives of phenylaminothiophenacetic acid, which are used in the pharmaceutical industry for the production of pharmaceutical compositions.

KNOWN TECHNICAL BACKGROUND

Phenylaminothiophenacetic acids are known from the U.S. Pat. No. 4,272,507 as agents with pronounced analgesic, antipyretic and, in particular, antphiogistic properties as is demonstrated by superior activity against acute and chronic inflammatory reactions. The disclosure of U.S. Pat. No. 4,272,507 is herein incorporated by reference in its entirety.

The international applications WO 9509831 and WO 0145703 describe nitric esters of derivatives of propionic acid and of certain selective COX-2 inhibitors, respectively, which are said to have anti-inflammatory activity and reduced adverse effects.

There is still a severe need of having drugs, which show pronounced anti-inflammatory activity together with good tolerance on the renal and/or respiratory and/or central nervous and/or autonomous system and/or, in particular, on the gastrointestinal and/or cardiovascular system, and/or which can be used at low dosages.

DESCRIPTION OF THE INVENTION

It has now been found that nitrate esters of derivatives of phenylaminothiophenacetic acid, which are described in greater details below, differ profoundly from the prior art compounds by incommensurable structural and pharmacological features and have unanticipated, surprising and particularly advantageous properties.

Thus the invention relates to compounds of formula I

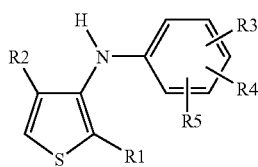

(I)

in which
either
R1 is hydrogen, chlorine, bromine or methyl,
R2 is —CH$_2$—C(O—O-A-O—NO$_2$, in which
A is 2-7C-alkylene,
R3 is hydrogen, halogen, 1-5C-alkyl, 1-5C-alkoxy or trifluoromethyl,
R4 is hydrogen, halogen, 1-5C-alkyl, 1-5C-alkoxy or trifluoromethyl,
R5 is hydrogen, halogen or 1-5C-alkyl,
or
R1 is —CH$_2$—C(O)—O-A-O—NO$_2$, in which
A is 2-7C-alkylene,
R2 is hydrogen, chlorine, bromine or methyl,
R3 is hydrogen, halogen, 1-5C-alkyl, 1-5C-alkoxy or trifluoromethyl,
R4 is hydrogen, halogen, 1-5C-alkyl, 1-5C-alkoxy or trifluoromethyl,
R5 is hydrogen, halogen or 1-5C-alkyl, and the salts, the solvates and the solvates of the salts of these compounds.

1-5C-Alkyl is a straight-chain or branched alkyl radical having 1 to 5 carbon atoms. Examples are the pentyl, butyl, isobutyl, sec-butyl, tert-butyl, propyl, isopropyl and preferably the ethyl and methyl radicals.

1-5C-Alkoxy is a radical which, in addition to the oxygen atom, contains a straight-chain or branched alkyl radical having 1 to 5 carbon atoms. Alkoxy radicals having 1 to 5 carbon atoms which may be mentioned in this context are, for example, the pentoxy, butoxy, isobutoxy, sec-butoxy, tert-butoxy, propoxy, isopropoxy and preferably the ethoxy and methoxy radicals.

Halogen within the meaning of the present invention is bromine, chlorine or fluorine.

2-7C-Alkylene represents straight-chain or branched 2-7C-alkylene radicals, for example the ethylene (—CH$_2$CH$_2$—), trimethylene (—CH$_2$CH$_2$CH$_2$—), tetramethylene (—CH$_2$CH$_2$CH$_2$CH$_2$—), 1,2-dimethylethylene [—CH(CH$_3$)—CH(CH$_3$)—], 1,1-dimethylethylene [—C(CH$_3$)$_2$—CH$_2$—], 2,2-dimethylethylene [—CH$_2$—C(CH$_3$)$_2$—], 1-methylethylene [—CH(CH$_3$)—CH$_2$—], pentamethylene (—CH$_2$CH$_2$CH$_2$CH$_2$CH$_2$—), hexamethylene (—CH$_2$CH$_2$CH$_2$CH$_2$CH$_2$CH$_2$—) and the heptamethylene (—CH$_2$CH$_2$CH$_2$CH$_2$CH$_2$CH$_2$CH$_2$—) radicals. Of the alkylene radicals A, the ethylene, the propylene, the butylene and the pentylene radicals, particularly the butylene radicals, are to be emphasized. Of the butylene radicals, the tetramethylene radical (—CH$_2$CH$_2$CH$_2$CH$_2$—) is particularly to be emphasized.

As salts in the scope of this invention, acid addition salts can be mentioned. Particular mention may be made of the pharmacologically tolerable salts of the inorganic or organic acids customarily used in pharmacy. Those are water-insoluble and, in particular, water-soluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embolic acid, stearic acid, toluenesulfonic acid, methanesulfonic acid or 3-hydroxy-2-naphthoic acid, where the acids are employed in sail preparation—depending on whether a mono- or polybasic acid is concerned and depending on which salt is desired—in an equimolar quantitative ratio or one differing therefrom.

On the other hand, salts with bases can be—depending on substitution—also suitable. As examples of salts with bases are mentioned the lithium, sodium, potassium, calcium, aluminum, magnesium, titanium, ammonium, meglumine or guanidinium salts, here, too, the bases being employed in salt preparation in an equimolar quantitative ratio or one differing therefrom.

The person skilled in the art knows on the base of his/her expert knowledge that depending on the substituents certain combinations of compounds of formula I and acids or bases mentioned above would lead to chemically less stable salts and/or to non salt formation. For example, in the case of the acid addition salts, this can apply in particular to those compounds of formula I, in which the amino nitrogen atom is sufficiently electron deficient, for example due to an electron withdrawing substitution pattern on the phenyl ring bonded to the amino nitrogen atom. Those compounds of formula I, which lead to chemically stable salts and/or to salt formation, in particular those compounds of formula I which do not have such a said electron deficiency being adverse for acid addition, are therefore preferred for salt formation.

Pharmacologically intolerable salts which can initially be obtained, for example, as process products in the preparation of the compounds according to the invention on an industrial scale are converted into pharmacologically tolerable salts by processes known to the person skilled in the art.

According to the knowledge of the person skilled in the art the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

One embodiment (embodiment a) of the invention relates to compounds of formula I, in which
R1 is hydrogen, chlorine, bromine or methyl,
R2 is —$CH_2$—C(O)—O-A-O—$NO_2$, in which
A is 2-7C-alkylene,
R3 is hydrogen, chlorine, methyl or trifluoromethyl,
R4 is hydrogen, chlorine, methyl or trifluoromethyl,
R5 is hydrogen or chlorine, and to the salts, the solvates and the solvates of the salts of these compounds.

Another embodiment (embodiment b) of the invention relates to compounds of formula I, in which
R1 is —$CH_2$—C(O)O—A-O—$NO_2$, in which
A is 2-7C-alkylene,
R2 is hydrogen or methyl,
R3 is hydrogen, chlorine, methyl or trifluoromethyl,
R4 hydrogen, chlorine, methyl or trifluoromethyl,
R5 is hydrogen or chlorine, and to the salts, the solvates and the solvates of the salts of these compounds.

Another embodiment (embodiment c) of the invention relates to compounds of formula I, in which A is tetramethylene (—$CH_2CH_2CH_2CH_2$—).

Another embodiment (embodiment d) of the invention relates to compounds of formula I, in which R3 is chlorine, R4 is chlorine and R5 is hydrogen.

Compounds of the embodiment a, which are to be emphasized, are those compounds of formula I, in which
R1 is hydrogen or chlorine,
R2 is —$CH_2$—C(O)—O-A-O—$NO_2$, in which
A is butylene,
R3 is chlorine, methyl or trifluoromethyl,
R4 is chlorine or methyl,
R5 is hydrogen or chlorine, and the salts, the solvates and the solvates of the salts of these compounds.

Compounds of the embodiment b, which are to be emphasized, are those compounds of formula I, in which
R1 is —$CH_2$—C(O)—O-A-O—$NO_2$, in which
A is butylene,
R2 is hydrogen,
R3 is chlorine, methyl or trifluoromethyl,
R4 chlorine or methyl,
R5 is hydrogen or chlorine, and the salts, the solvates and the solvates of the salts of these compounds.

Compounds of the embodiment a, which are particularly to be emphasized, are those compounds of formula I, in which
R1 is hydrogen,
R2 is —$CH_2$—C(O)—O-A-O—$NO_2$, in which
A is butylene,
R3 is chlorine or methyl,
R4 is chlorine,
R5 is hydrogen, and the salts, the solvates and the solvates of the salts of these compounds.

Compounds of the embodiment b, which are particularly to be emphasized, are those compounds of formula I, in which
R1 is —$CH_2$—C(O)—O-A-O—$NO_2$, in which
A is butylene,
R2 is hydrogen,
R3 is chlorine or methyl,
R4 chlorine,
R5 is hydrogen, and the salts, the solvates and the solvates of the salts of these compounds.

A preferred compound according to the invention is this of formula I, in which
R1 is hydrogen,
R2 is $CH_2$—(O)—O-A-O—$NO_2$, in which
A is tetramethylene,
R3 is chlorine,
R4 is chlorine,
R5 is hydrogen, and the solvates of this compound.

A preferred embodiment of the invention is embodiment d, in which R3 and R4 are attached in the ortho positions with respect to the binding position in which the phenyl ring is bonded to the nitrogen atom.

A further preferred embodiment of the invention is embodiment a.

A more preferred embodiment of the invention is embodiment a, in which R1 is hydrogen.

Exemplary representative compound according to the invention is [4-(2,6-Dichlorophenylamino)-thiophen-3-yl]-acetic acid 4-nitrooxybutyl ester and its solvates.

The compounds of formula I according to the invention can be prepared, for example, as described by way of example in the following examples according to those synthesis routes shown in reaction scheme 1 and specified below or using analogous or similar process steps. The starting compounds of formulae III, in which R3, R4 and R5 have the meanings mentioned above, R1 is hydrogen, chlorine, bromine or methyl and M represents a suitable base or a suitable metal atom (e.g. an alkali metal atom, preferably a sodium atom), and VI, in which R3, R4 and R5 have the meanings mentioned above, R2 is hydrogen, chlorine, bromine or methyl and M represents said suitable base or suitable metal atom, and their preparation are known from U.S. Pat. No. 4,272,507 or they can prepared similarly or analogously to art-known process steps, for example they can be obtained as isolated or non-isolated Intermediates starting from the corresponding acids, which are also known from U.S. Pat. No. 4,272,507, by reaction with suitable inorganic or organic bases (e.g. alkali carbonates).

In a further preferred embodiment of this invention, the starting compounds of formulae III or VI are those compounds, which are specifically disclosed in the U.S. Pat. No. 4,272,507.

In a further more preferred embodiment of this invention, the starling compounds of formulae III or VI are those compounds, which are disclosed in the U.S. Pat. No. 4,272,507 as preferred compounds and/or as examples.

Reaction scheme 1 shows by way of example the preparation of compounds of formula I, in which R1, R2, R3, R4, R5 and A have the meanings mentioned above, starting either from compounds of formula III, in which R3, R4 and R5 have the meanings indicated above, R1 is hydrogen, chlorine, bromine or methyl and M represents said suitable base or suitable metal atom, or from compounds of formula VI, in which R3, R4 and R5 have the meanings indicated above, R2 is hydrogen, chlorine, bromine or methyl and M represents said suitable base or suitable metal atom, by substitution reaction with compounds of the formula IV, in which A has the meanings given above, X is a suitable leaving group (e.g. chlorine, iodine or, preferably, bromine) and Y is hydroxyl or a further suitable leaving group with the same or different meaning as X, to obtain in a first step the corresponding compounds of the formulae II or V. Said substitution reaction can be carried out as described in the following examples or in an art-known manner in a suitable solvent (e.g. acetone) at elevated temperature or at boiling temperature of the solvent used.

Abovementioned compounds of formula IV are known or can be obtained in a manner habitual per se to the person skilled in the art.

desired nitrate ester compounds of formula I, in which R1, R2, R3, R4, R5 and A have the meanings mentioned above. Said substitution reaction can be carried out as described in the following examples or in a manner known to one of ordinary skill in the art in a suitable solvent (e.g. acetonitrile) at elevated temperature or at boiling temperature of the solvent used.

Those compounds of formulae II, in which A, R3, R4 and R5 have the meanings indicated above, R1 is hydrogen, chlorine, bromine or methyl and Y is hydroxyl, or V, in which A, R3, R4 and R5 have the meanings indicated above, R2 is hydrogen, chlorine, bromine or methyl and Y is hydroxyl, respectively, can be also processed into the desired nitrate ester compounds of formula I, in which R1, R2, R3, R4, R5 and A have the meanings mentioned above. This conversion can be carried out in a manner habitual per se to one of ordinary skill in the art, for example according to an esterifi- Reaction scheme 1:

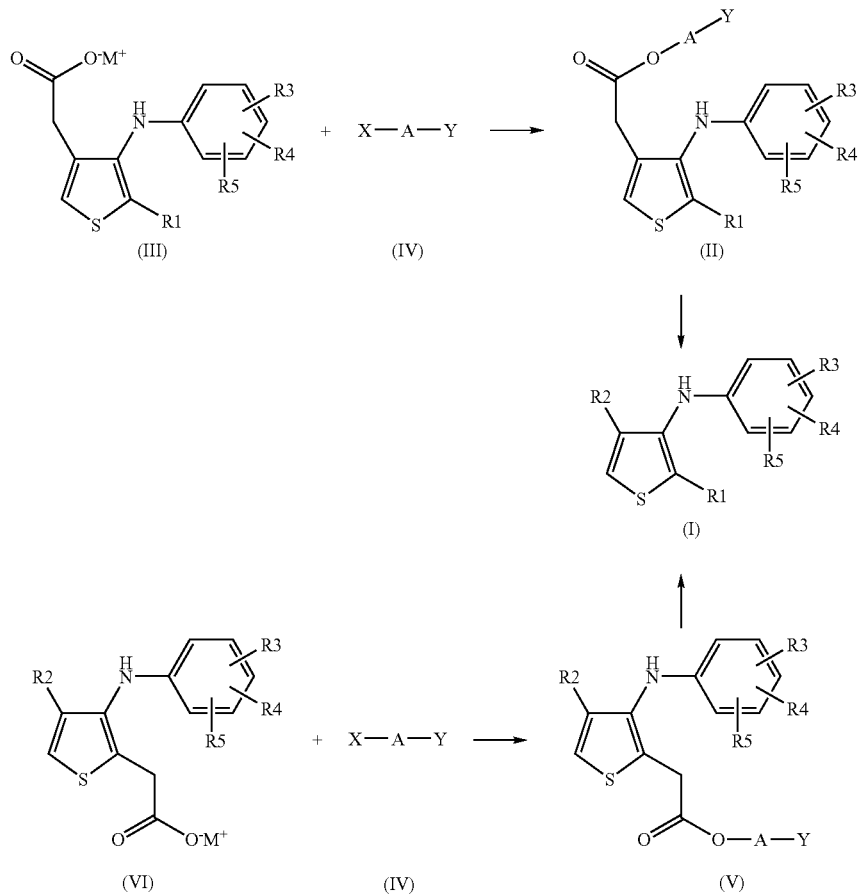

In a second step those compounds of formulae II, in which A, R3, R4 and R5 have the meanings indicated above, R1 is hydrogen, chlorine, bromine or methyl and Y represents said suitable leaving group, or V, in which A, R3, R4 and R5 have the meanings indicated above, R2 is hydrogen, chlorine, bromine or methyl and Y represents said suitable leaving group, respectively, can be converted by substitution reaction with suitable nitrate compounds (e.g. silver nitrate) into the cation reaction of nitric acid (such as, for example, described in J. March, Advanced Organic Chemistry, $3^{rd}$ ed., Wiley, 1985, p. 357f).

Compounds of formulae II, in which A, R3, R4 and R5 have the meanings indicated above, R1 is hydrogen, chlorine, bromine or methyl and Y is said suitable leaving group or hydroxyl, or V, in which A, R3, R4 and R5 have the meanings indicated above, R2 is hydrogen, chlorine, bromine or methyl and Y is said suitable leaving group or hydroxyl, are also accessible by esterification reaction of the corresponding free acid compounds of formulae III and VI with compounds of formula VII, in which A has the meanings given above and Y is hydroxyl or a suitable leaving group. More specifically, this reaction is carried out in the presence of condensation reagents or ester bond linking reagents known to the person skilled in the art Exemplary reagents which may be mentioned in this connection are, for example, suitable acids, the carbodiimides (e.g. dicyclohexylcarbodiimide or 1-ethyl-3-(3-dimethyl-aminopropyl)carbodiimide hydrochloride) or N,N'-carbonyldiimidazole.

HO-A-Y (VII)

Furthermore, the desired compounds of formulae II or V can be also prepared by reaction of said compounds of formula VII with compounds of formulae VIII, in which R1, R3, R4 and R5 have the meanings indicated above and Z represents a suitable leaving group, preferably a chlorine atom, or IX, in which R2, R3, R4 and R5 have the meanings indicated above and Z represents a suitable leaving group, preferably a chlorine atom, in a manner customary per se to the skilled person.

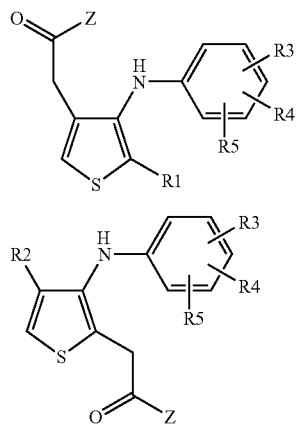

Compounds of formula VII are known or can be prepared according to known methods.

Compounds of formulae VII and IX are obtainable by art-known processes from the corresponding free acid compounds, which are already described in U.S. Pat. No. 4,272,507.

Alternatively, compounds of formula I according to the present invention can be also prepared from compounds of formula X, in which A has the meanings given above and W is a suitable leaving group, e.g. chlorine, iodine or, preferably, bromine, and said compounds of formulae III or VI in a manner known to the skilled person or as specified above.

W-A-O—NO$_2$ (X)

In further alternatives, said free acid derivatives of compounds of formulae III or VI or said compounds of formulae VIII or IX can be also reacted with compounds of the formula XI, in which A has the above-mentioned meanings, to give in an art-known manner or analogously or similarly as described above the desired compounds of formula I.

HO-A-O-NO$_2$ (XI)

Compounds of formulae X and XI are known or can be prepared according to methods which are known to the skilled person or described in greater detail above, or analogously or similarly thereto.

It is evident to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in T. Greene and P. Wuts, "Protective Groups in Organic Synthesis" (John Wiley & Sons, Inc. 1999, 3$^{rd}$ Ed.) or in P. Kocienski, "Protecting Groups (Theme Foundations Organic Chemistry Series N Group" (Theme Medical Publishers, 2000).

The substances according to the invention are isolated and purified in a manner known per se, e.g. by distilling off the solvent in vacuo and recrystallizing the residue obtained from a suitable solvent or subjecting it to one of the customary purification methods, such as column chromatography on a suitable support material.

Salts are obtained by dissolving the free compound in a suitable solvent (for example a ketone like acetone, methylethylketone, or methylisobutylketone, an ether, like diethyl ether, tetrahydrofuran or dioxane, a chlorinated hydrocarbon, such as methylene chloride or chloroform, or a low molecular weight aliphatic alcohol, such as ethanol, isopropanol) which contains the desired acid, or to which the desired acid is then added. The salts are obtained by filtering, reprecipitating, precipitating with a non-solvent for the addition salt or by evaporating the solvent. Salts obtained can be converted by basification into the free compounds which, in turn, can be converted into salts. In this manner, pharmacologically non-tolerable salts can be converted into pharmacologically tolerable salts.

The person skilled in the art knows on the basis of his/her knowledge and of the basis of the disclosure of the present invention how to find further alternative embodiments according to the present invention. All these other possible and/or suitable alternative embodiments are also part of the scope of this invention.

The following examples illustrate the invention in greater detail, without restricting it. As well, further compounds of formula I, of which the preparation is explicitly not described, can be prepared in an analogous or similar way or in a way which is known by a person skilled in the art using customary preparation methods.

In the examples, h stands for hour(s), EF for empirical formula, calc. for calculated, fnd. for found. The compounds, which are mentioned in the examples as well as their solvates, are preferred compounds of the invention.

EXAMPLES

Final Products

1. [4-(2,6-Dichlorophenylamino)-thiophen-3-yl]-acetic acid 4-nitrooxybutyl ester A solution of 1.75 g of silver nitrate in 18 ml of acetonitrile is added to 3.0 g of [4-(2,6-dichlorophenyl-amino)thiophen-3-yl]-acetic acid 4-bromobutyl ester (compound A1) in 11 ml of acetonitrile. The solution is stirred at 85° C. for 5 h, filtered and concentrated under reduced pressure. The residue is treated with dichloromethane and filtered. The organic layer is washed with water, dried using sodium sulfate and concentrated. The residue is chromatographed on silica gel using a mixture of petroleum ether (low)/ethyl acetate=5/1 to give 2.1 g of the the compound as an oil.

EF: $C_{18}H_{16}Cl_2N_2O_5S$
Elemental analysis:

| cal.: | C | 45.83 | H | 3.85 | N | 6.68 | S | 7.65 | Cl | 16.91 |
|---|---|---|---|---|---|---|---|---|---|---|
| fnd.: | | 46.05 | | 3.94 | | 6.71 | | 7.41 | | 17.08 |

A1. [4-(2,6-Dichlorophenylamino)-thiophen-3-yl]-acetic acid 4-bromobutyl ester 5.0 g of sodium [4-(2,6-dichloro-phenylamino)-thiophen-3-yl]-acetate (preparation described in U.S. Pat. No. 4,272,507) are added in portions to a solution of 28.4 ml of 1,4dibromobutane in 250 ml of acetone at room temperature. The solution is refluxed for 5 h, filtered and concentrated under reduced pressure. The residue is chromatographed on silica gel using petroleum ether (low) and subsequently a mixture of petroleum ether (low)/ethyl acetate=7/1 to give 3.0 g of the title compound as an oil.

Commercial Applicability

The compounds according to the invention have miscellaneous valuable pharmacological properties which make them commercially utilizable. Thus, for example, their excellent properties as cytoprotective nitric oxide releasing non-steroidal anti-inflammatory drugs (NO-NSAID) and as cyclooxygenase inhibiting nitric oxide donors (CINOD) allow them to be used in veterinary and/or, particularly, in human medicine as active principles for preventing and/or treating of, for example, inflammation, pain (both chronic and acute), fever and other cyclooxygenase mediated disorders, for facilitating wound healing and for gastro-protecting, for decreasing or reversing renal or other toxicity (e.g. kidney toxicity) and for providing of medicaments of improved tolerance at the renal level, the respiratory level, the level of the central nervous or autonomous system or, in particular, at the gastrointestinal or cardiovascular level.

Special isoforms of the abovementioned cyclooxygenase, which are preferred to be mentioned in this connection, include in particular cyclooxygenase-1 (COX-1) and cyclooxygenase-2 (COX-2) but also cyclooxygenase-3 (COX-3). Each of these cyclooxygenase isoforms (COX-1, COX-2 and COX-3) can be regarded as a valuable pharmacological target of the compounds according to this invention.

With respect to the compounds according to the present invention, a target for inhibition, which is to be emphasized with regard to favourable antinflammatory effects, represents the cyclooxygenase-2. Inter alia due to their excellent NO-donor abilities, the compounds according to the invention show also beneficial tolerance and/or an advantageous and desired therapeutic profile.

Moreover, the compounds according to the present invention can be used to provide agents, which feature, as a whole, inhibition of cyclooxygenase-1 and cyclooxygenase-2 with little selectivity for either isoform but without the adverse effects commonly associated with the inhibition of the cyclooxygenase-1.

Still further, the compounds according to the invention can be used as agents, which show—in comparison to the underlying non-nitrated parent drugs (e.g. Eltenac)—improved properties.

Thus, the compounds according to the invention can be used, for example as analgesics in the treatment of pain, including but not limited to headaches, migraines, postoperative pain, dental pain, muscular pain and pain resulting from cancer, as antipyretics in the treatment of fever, including but not limited to rheumatic fever, symptoms associated with influenza or other viral infections, common cold, low back and neck pain, dysmenorrhea, headache, toothache, sprains, strains, myositis, neuralgia and synovits, or as an anti-inflammatory in the treatment of arthritis, including but not limited to rheumatoid arthritis, degenerative joint disease (osteoarthritis), spondyloarthritis, gouty arthritis, systemic lupus erythematosus and juvenile arthritis.

Furthermore, inter alia due to their ability to release cytoprotective nitric oxide, the compounds according to the invention can be used to facilitate wound healing in the therapy and/or prophylaxis of lesions, such as, for example, ulcers (e.g. gastric ulcers, duodenal ulcers, gastritis and the like), cuts, burns and the like.

Additionally, inter alia due to their ability to release cytoprotective nitric oxide, the compounds according to the invention can be used in the prophylaxis and therapy of gastrointestinal inflammatory diseases and gastrointestinal disorders such as, for example, inflammatory bowel disease, Crohn's disease, gastritis, irritable bowel syndrome, ulcerative colitis, peptic ulcers, gastric ulcers, duodenal ulcers, stress ulcers, gastric hyperacidity, dyspepsia, gastroparesis, Zollinger-Ellison syndrome, gastroesophageal reflux disease, bacterial infections (including, for example, *Helicobacter Pylori* associated diseases), short-bowel (anastomosis) syndrome, hypersecretory states associated with systemic mastocytosis or basophilic leukaemia and hyperhistaminemia and bleeding peptic ulcers that result, for example, from neurosurgery, head injury, severe body trauma or burns.

There are a number of pathophysiological situations which among others are characterized by abnormal and/or pathological levels of cyclooxygenase(s) (COX). In this connection, cyclooxygenase-1 (COX-1), cyclooxygenase-2 (COX-2) and cyclooxygenase-3 (COX-3) mediated disorders are to be mentioned, whereby those disorders characterized by elevated levels of COX-2 are particularly to be indicated. On account on their properties as cyclooxygenase inhibiting nitric oxide donors, the compounds according to the invention can be employed, without being limited, for the therapy and/or prophylaxis of the following diseases: angiogenesis, arthritis, asthma, bronchitis, menstrual cramps, pre-mature labor, tendinitis, bursitis; skin-related conditions, such as, for example, psoriasis, eczema, surface wounds, bums and dermatitis; post-operative inflammation including from ophthalmic surgery, such as, for example, cataract surgery and refractive surgery, and the like; treatment of neoplasia, such as, for example, brain cancer, bone cancer, epithelial cell-derived neoplasia (epithelial carcinoma), such as, for example, basal cell carcinoma, adenocarcinoma, gastrointestinal cancer, such as, for example, lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that effect epithelial cells throughout the body, benign and cancerous tumors, growths, polyps, adenomatous polyps, including, but not limited to, familial adenomatous, polyposis, fibrusis resulting from radiation therapy, and the like; treatment of inflammatory processes in diseases, such as, for example, vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcert's syndrome, polymyositis, gingivitis, nephritis, hypersensitivity, swelling occurring after injury, myocardial ischemia, and the like; treatment of ophthalmic diseases and disorders, such as, for example, retinitis, retinopathies, uveitis, ocular photophobia, acute injury to the eye tissue, glaucoma, inflammation of the eye and elevation of intraocular pressure and the like; treatment of pulmonary inflammation, such as, for example, those associated with viral infections and cystic fibrosis, and the like; treatment of certain central nervous system disorders, such as, for example, cortical dementias including Alzheimer's disease, vascular dementia, multi-infarct dementia, pre-senile dementia, alcoholic dementia, senile dementia, and central nervous system damage resulting from stroke, ischemia and trauma, and the like; treatment of allergic rhinitis, respiratory distress syndrome, endotoxin shock syndrome, atherosclerosis; treatment of inflammations and/or microbial infections including, for example, inflammations and/or infections of the eyes, ears, nose, throat, and/or skin; treatment and/or prevention of cardiovascular disorders, such as, for example, coronary artery disease, aneurysm, arteriosclerosis, atherosclerosis, including, but not limited to, cardiac transplant atherosclerosis, myocardial infarction, ischemia, embolism, stroke, thrombosis, hypertension, venous thrombosis, thromboembolism, thrombotic occlusion and reclusion, restenosis, angina, unstable angina, shock, heart failure, coronary plaque inflammation, bacterial-induced inflammation, such as, for example, Chlamydia-induced inflammation, viral induced inflammation, inflammation associated with surgical procedures, such as, for example, vascular grafting, coronary artery bypass surgery, revascularization procedures, such as, for example, angioplasty, stent placement, endarterectomy, vascular procedures involving arteries, veins, capillaries, and the like; treatment and/or prevention of urinary and/or urological disorders, such as, for example, incontinence and the like; treatment and/or prevention of endothelial dysfunctions, such as, for example, diseases accompanying these dysfunctions, endothelial damage from hypercholesterolemia, endothelial damage from hypoxia, endothelial damage from mechanical and chemical noxae, especially during and after drug, and mechanical reopening of stenosed vessels, for example, following percutaneous transluminal angiography (PTA) and percuntaneous transluminal coronary angiography (PTCA), endothelial damage in postinfarction phase, endothelium-mediated reocclusion following bypass surgery, blood supply disturbances in peripheral arteries, as well as, cardiovascular diseases, and the like; preservation of organs and issues, such as, for example, for organ transplants, and the like; inhibition and/or prevention of activation, adhesion and infiltration of neutrophils at the site of inflammation; inhibition and/or prevention of platelet aggregation. The compounds and compositions of the present invention can also be used as a pre-anesthetic medication in emergency operations to reduce the danger of aspiration of acidic gastric contents.

In this connection, on account of their excellent pharmacological properties, the special utilizability of the compounds according to the present invention in the treatment and/or prevention of pain, osteoarthritis, rheumatoid arthritis and Alzheimer's disease is particularly to be emphasized.

Moreover, in a further embodiment of the present invention the non-cyclooxygenase mediated properties of the compounds according to the present invention are to be worthy to be mentioned. In particular, the effects of the compounds according to this invention on the modulation of the cytokine pattern (in particular on the inhibition of inflammatory cytokine induction), on the peroxisome proliferator-activated receptor alpha (PPARalpha), on the peroxisome proliferator-activated receptor gamma (PPARgamma) and on the peroxisome proliferator-activated receptor delta (PPARdelta) are to be emphasized in this connection and to be accentuated as valuable for therapy and/or prophylaxis of the abovementioned diseases, disorders or illnesses.

Another embodiment of the invention provides methods for therapy or prophylaxis of mammals, in particular humans, which are in need thereof, particularly those, which are suffering from diseases, disorders or illnesses, especially from one of the abovementioned illnesses. Methods according to the invention, which can be mentioned in this connection, are, for example, methods for preventing and/or treating of inflammation, pain (both chronic and acute), fever and other cyclooxygenase mediated disorders, methods for therapy which are, inter alia, targeted on peroxisome proliferator-activated receptor alpha (PPARalpha) and/or on peroxisome proliferator-activated receptor gamma (PPARgamma) and/or on peroxisome proliferator-activated receptor delta (PPARdelta), methods for facilitating wound healing and for gastroprotecting, methods for decreasing or reversing renal or other toxicity (e.g. kidney toxicity) and methods for decreasing and/or preventing gastrointestinal disorders and improving the gastro-intestinal properties of underlying non-nitrated parent drugs. These methods comprise administering to the patient in need thereof a therapeutically active and pharmaceutically effective and tolerable amount of one or more of the compounds according to the invention.

The invention moreover relates to the compounds according to the invention for use in the treatment or prophylaxis of illnesses, especially the illnesses mentioned.

The invention further relates to the use of the compounds according to the invention for the manufacture of pharmaceutical compositions which are employed for the treatment or prevention of inflammatory diseases.

In this connection, the term "inflammatory diseases" refers in the meaning of this invention to those diseases, illnesses or disorders which are known to the person skilled in the art and/or which are mentioned in the description of this invention.

The invention also relates to pharmaceutical compositions for the treatment or prevention of the diseases, illnesses or disorders mentioned, which comprise one or more of the compounds according to the invention.

The compounds and compositions of the present invention may also be used in a fixed or free combination together with other suitable substances for co-therapies and/or prophylaxis of the abovementioned illnesses. Said suitable substances comprise for example—without being restricted to—opioids and other analgesics, inducible nitric oxide synthase inhibitors, steroids, nonsteroidal antiinflamma-tory drugs (NSAID), cyclooxygenase-2 (COX-2) inhibitors, 5-lipoxygenase (5-LO) inhibitors, leukotriene $B_4$ ($LTB_4$) receptor antagonists, leukotriene $A_4$ ($LTA_4$) hydrolase inhibitors, 5-HT agonists, 3-hydroxy-3-methylglutaryl coenzyme A (HMG-CoA) inhibitors, H2 antagonists, antineoplastic agents, antiplatelet agents, antitussives, decongestants, diuretics, sedating or non-sedating anti-histamine, *Helicobacter pylori* inhibitors, reversible and irreversible proton pump inhibitors (such as those described in literature, for example in Goodman and Gilman, The Pharmacological Basis of Therapeutics, $9^{th}$ Edition, McGraw-Hill, 1995, p. 901-915 or in the Merck index on CD-ROM, $12^{th}$, Edition, Version 12:1, 1996, whereby omeprazole, lansoprazole, rabeprazole and pantoprazole are particularly mentioned), isoprostane inhibitors, and, optionally, at least one compound that donates, transfers or releases nitric oxide, or elevates levels of endogenous endothelium-derived relaxing factor (EDRF) or nitric oxide, or is a substrate for nitric oxide synthase. The compounds can be administered separately, sequentially or simultaneously.

In this connection, the present invention also provides pharmaceutical kits comprising one or more of the compounds according to the invention and one or more of the abovementioned suitable substances for co-therapies. Associated with such kits can be additional therapeutic agents or compositions, devices for administering and notices in form prescribed by a governmental agency regulating the manufacture, use or sale of pharmaceuticals or biological products which reflects approval by the agency of manufacture, use or sale for humans.

Further, the present invention is also directed to methods for therapy or prophylaxis of the abovementioned illnesses, diseases or disorders comprising administering to a mammal, particularly a human, in need thereof a therapeutically active and pharmaceutically effective and tolerable amount of one or more of the compounds according to the invention.

Furthermore, the present invention is also directed to methods for therapy or prophylaxis of the abovementioned illnesses, diseases or disorders comprising administering separately, sequentially or simultaneously to a mammal, particularly a human, in need thereof a therapeutically active and pharmaceutically effective and tolerable amount of one or more of the compounds according to the invention and one or more of the abovementioned substances which are suitable for co-therapies.

Additionally, the present invention provides methods for improving the therapeutic profile and/or the tolerance, particularly on the gastrointestinal and/or cardiovascular system, of the compounds disclosed in U.S. Pat. No. 4,272,507 by administering to the patient in need thereof a therapeutically active and pharmaceutically effective and tolerable amount of one or more compounds according to the invention.

Further, the present invention disclose methods for improving the therapeutic profile and/or the tolerance (e.g. on the gastrointestinal level) of a suitable antiinflammatory agent, such as, for example, the active principle of a nonsteroidal anti-inflammatory drug (NSAID) known to the person skilled in the art, which inhibits either both cyclooxygenase-1 and cyclooxygenase-2 with little selectivity for either isoform or is COX-1 selective, comprising subjecting said antiinflammatory agent to the same, analogous or similar structural conversions disclosed and specified in the present invention.

The pharmaceutical compositions are prepared by processes which are known per se and familiar to the person skilled in the art. As pharmaceutical compositions, the compounds according to the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries or excipients which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the pharmaceutical compositions according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of disorders of the respiratory tract, the compounds according to the invention are preferably also administered by inhalation in the form of an aerosol; the aerosol particles of solid, liquid or mixed composition preferably having a diameter of 0.5 to 10 µm, advantageously of 2 to 6 µm.

Aerosol generation can be carried out, for example, by pressure-driven Jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular administered in the form of those pharmaceutical compositions which are suitable for topical application. For the production of the pharmaceutical compositions, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary per se. Topical application forms (such as ointments) for the treatment of dermatoses thus contain the active compounds in a concentration of, for example, 0.1-99%. The dose for administration by inhalation is customarily between 0.1 and 10 mg per day. The customary dose in the case of systemic therapy (p.o.) is between 0.3 and 30 mg/kg per day, (I.v.) is between 0.3 and 30 mg/kg/h.

Biological Investigations

In Vitro Cox-2 Assay

Fresh blood was collected in heparinized (8 U/ml, Roche, Switzerland) tubes by venipuncture from both male and female volunteers with consent The subjects had no apparent inflammatory conditions and had not taken any NSAIDs for the last 7 days prior to blood collection. 450 µl aliquots of blood were incubated in deep wells with either 1 µl vehicle (DMSO) or 1 μl of test compound at a final concentration varying from 100 μM-10 nM for 15 min at 37° C. This was followed by incubation of the blood with 50 μl lipopolysaccharide (LPS, Sigma, Germany) 10 μg/ml in 0.1% Hydroxylamine/PBS (Sigma) for 24 h. At the end of incubation the blood was centrifuged at 2000 g for 5 min and 100-150 ml supernatant was assayed for $PGE_2$ using a immunoassay kit (RD Systems, Germany)

In Vitro Cox-1 Assay

Fresh blood was collected into vacutainers containing no anticoagulants. Aliquots of 450 μl were immediately transferred to deep well plates preloaded with 1 μl of either DMSO or a test compound at final concentration of 100 μM-10 nM. In addition 50 μl of Hydroxylamine/PBS were added and the tubes were vortexed and incubated at 37° C. for 1 h to allow the blood to clot. At the end of incubation, serum was obtained by centrifugation (2000 g/5 min) and the supernatant was assayed for $TxB_2$ using a immunoassay kit (RD Systems, Germany) according to the manufactures instruction.

Calculation

The data were analysed from 2-3 independent dose response curves with a nonlinear estimation program using GRAPHPAD/Prism and given as $pIC_{50}$ Results The inhibitory value determined for an exemplary compound according to the invention follow from the following table A, in which the compound number correspond to the example number.

Inhibition of COX-1 and COX-2 activity [measured as $pIC_{50}$]:

| Compound | COX-1 | COX-2 |
|----------|-------|-------|
| 1 | 7.05 | 7.14 |

The invention claimed is:

1. A compound of formula I

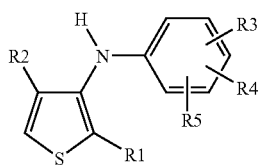

(I)

in which
either
R1 is hydrogen, chlorine, bromine or methyl,
R2 is —CH₂—C(O)—O-A-O—NO₂, in which
A is 2-7C-alkylene,
R3 is hydrogen, halogen, 1-5C-alkyl, 1-5C-alkoxy or trifluoromethyl,
R4 has one of the meanings of R3,
R5 is hydrogen, halogen or 1-5C-alkyl,
or
R1 is —CH₂—C(O)—O-A-O—NO₂, in which
A is 2-7C-alkylene,
R2 is hydrogen, chlorine, bromine or methyl,
R3 is hydrogen, halogen, 1-5C-alkyl, 1-5C-alkoxy or trifluoromethyl,
R4 has one of the meanings of R3,
R5 is hydrogen, halogen or 1-5C-alkyl, or a hydrate, solvate, salt, hydrate of a salt or solvate of a salt thereof.

2. A compound of formula I according to claim 1, in which either
R1 is hydrogen, chlorine, bromine or methyl,
R2 is —CH₂—C(O)—O-A-O—NO₂, in which
A is 2-7C-alkylene,
R3 is hydrogen, chlorine, methyl or trifluoromethyl,
R4 is hydrogen, chlorine, methyl or trifluoromethyl,
R5 is hydrogen or chlorine,
or
R1 is —CH₂—C(O)—O-A-O—NO₂, in which
A is 2-7C-alkylene,
R2 is hydrogen or methyl,
R3 is hydrogen, chlorine, methyl or trifluoromethyl,
R4 hydrogen, chlorine, methyl or trifluoromethyl,
R5 is hydrogen or chlorine, or a hydrate, solvate, salt, hydrate of a salt or solvate of a salt thereof.

3. A compound of formula I according to claim 1, in which either
R1 is hydrogen or chlorine,
R2 is —CH₂—C(O)—O-A-O—NO₂, in which
A is butylene,
R3 is chlorine, methyl or trifluoromethyl,
R4 is chlorine or methyl,
R5 is hydrogen or chlorine,
or
R1 is —CH₂—C(O)—O-A-O—NO₂, in which
A is butylene,
R2 is hydrogen,
R3 is chlorine, methyl or trifluoromethyl,
R4 chlorine or methyl,
R5 is hydrogen or chlorine, or a hydrate, solvate, salt, hydrate of a salt or solvate of a salt thereof.

4. A compound of formula I according to claim 1, in which either
R1 is hydrogen,
R2 is —CH₂—C(O)—O-A-O—NO₂, in which
A is butylene,
R3 is chlorine or methyl,
R4 is chlorine,
R5 is hydrogen,
or
R1 is —CH₂—C(O)—O-A-O—NO₂, in which
A is butylene,
R2 is hydrogen,
R3 is chlorine or methyl,
R4 chlorine,
R5 is hydrogen, or a hydrate, solvate, salt, hydrate of a salt or solvate of a salt thereof.

5. A compound of formula I according to claim 1, in which
R1 is hydrogen,
R2 is —CH₂—C(O)—O-A-O—NO₂, in which
A is tetramethylene,
R3 is chlorine,
R4 is chlorine,
R5 is hydrogen, or a hydrate, solvate, salt, hydrate of a salt or solvate of a salt thereof.

6. A pharmaceutical composition comprising a compound of formula I according to claim 1, or a hydrate, solvate, salt, hydrate of a salt or solvate of a salt thereof, together with a pharmaceutically acceptable auxiliary and/or excipient.

7. A method of treating an illness, disorder or disease in a mammal comprising administering to said mammal a therapeutically effective amount of a compound of formula I according to claim 1, or a hydrate, solvate, salt, hydrate of a salt or solvate of a salt thereof; wherein the illness, disorder, or disease is selected from the group consisting of: pain, inflammatory diseases and disorders, gastrointestinal inflammatory diseases, gastrointestinal disorders, fever, wounds, lesions, asthma, bronchitis, menstrual cramps, premature labor, tendinitis, bursitis, neoplasia, ophthalmic diseases and disorders, central nervous system disorders, central nervous system disorders, and central nervous system damage.

* * * * *

UNITED STATES PATENT AND TRADEMARK OFFICE
CERTIFICATE OF CORRECTION

| | | |
|---|---|---|
| PATENT NO. | : 7,524,973 B2 | |
| APPLICATION NO. | : 10/545414 | |
| DATED | : April 28, 2009 | |
| INVENTOR(S) | : Beate Schmidt | |

It is certified that error appears in the above-identified patent and that said Letters Patent is hereby corrected as shown below:

Claim 1, Column 16, Lines 2-3:
Please delete "or a hydrate, solvate, salt, hydrate of a salt or solvate of a salt thereof." and replace with:
-- or a salt thereof. --

Claim 2, Column 16, Line 17:
Please delete "R4 hydrogen, chlorine, methyl or trifluoromethyl," and replace with:
-- R4 is hydrogen, chlorine, methyl or trifluoromethyl, --

Claim 2, Column 16, Lines 18-19:
Please delete "or a hydrate, solvate, salt, hydrate of a salt or solvate of a salt thereof." and replace with:
-- or a salt thereof. --

Claim 3, Column 16, Line 33:
Please delete "R4 chlorine or methyl," and replace with:
-- R4 is chlorine or methyl, --

Claim 3, Column 16, Lines 34-35:
Please delete "or a hydrate, solvate, salt, hydrate of a salt or solvate of a salt thereof." and replace with:
-- or a salt thereof. --

Claim 4, Column 16, Line 49:
Please delete "R4 chlorine," and replace with:
-- R4 is chlorine, --

Claim 4, Column 16, Lines 50-51:
Please delete "or a hydrate, solvate, salt, hydrate of a salt or solvate of a salt thereof." and replace with:
-- or a salt thereof. --

Claim 4, Column 16, Lines 58-59:
Please delete "or a hydrate, solvate, salt, hydrate of a salt or solvate of a salt thereof." and replace with:
-- or a salt thereof. --

UNITED STATES PATENT AND TRADEMARK OFFICE
CERTIFICATE OF CORRECTION

PATENT NO. : 7,524,973 B2
APPLICATION NO. : 10/545414
DATED : April 28, 2009
INVENTOR(S) : Beate Schmidt It is certified that error appears in the above-identified patent and that said Letters Patent is hereby corrected as shown below:

Claim 6, Column 16, Lines 61-62:
Please delete "or a hydrate, solvate, salt, hydrate of a salt or solvate of a salt thereof," and replace with:
-- or a salt thereof, --

Claim 7, Column 16, Line 64:
Please delete "an illness, disorder or disease" and replace with:
-- pain --

Claim 7, Column 16, Line 67 and Column 17, Line 1:
Please delete "or a hydrate, solvate, salt, hydrate of a salt or solvate of a salt thereof;" and replace with:
-- or a salt thereof. --

Claim 7, Column 17, Lines 1-5 and Column 18, Lines 1-3:
Please delete "wherein the illness, disorder, or disease is selected from the group consisting of: pain, inflammatory diseases and disorders, gastrointestinal inflammatory diseases, gastrointestinal disorders, fever, wounds, lesions, asthma, bronchitis, menstrual cramps, premature labor, tendinitis, bursitis, neoplasia, ophthalmic diseases and disorders, central nervous system disorders, central nervous system disorders, and central nervous system damage."

Signed and Sealed this

Thirtieth Day of June, 2009

JOHN DOLL
*Acting Director of the United States Patent and Trademark Office*